United States Patent
Lyles et al.

(10) Patent No.: US 6,544,324 B1
(45) Date of Patent: *Apr. 8, 2003

(54) BONE CEMENT COMPOSITIONS COMPRISING FUSED FIBROUS COMPOUNDS

(75) Inventors: Mark B. Lyles, San Antonio, TX (US); Kevin D. Rathbun, Mountain View, CA (US)

(73) Assignee: Materials Evolution and Development USA Inc., San Antonio, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/952,770

(22) Filed: Sep. 14, 2001

Related U.S. Application Data

(63) Continuation of application No. 09/174,753, filed on Oct. 19, 1998, now Pat. No. 6,291,547, which is a continuation of application No. 08/684,251, filed on Jul. 19, 1996, now abandoned, which is a continuation-in-part of application No. 08/386,305, filed on Feb. 8, 1995, now Pat. No. 5,621,035.

(51) Int. Cl.[7] ............ A61L 42/02; A61L 24/04; A61L 24/08
(52) U.S. Cl. ............ 106/35; 623/26.62; 523/116; 523/115; 424/423
(58) Field of Search ............ 623/23.62; 106/35; 523/116, 115; 424/423

(56) References Cited

U.S. PATENT DOCUMENTS

| | | |
|---|---|---|
| 3,721,644 A | 3/1973 | Stoffey et al. |
| 4,064,566 A | 12/1977 | Fletcher et al. |
| 4,239,113 A | 12/1980 | Gross et al. |
| 4,365,357 A | 12/1982 | Draenert |
| 4,381,918 A | 5/1983 | Ehrnford |
| 4,392,828 A | 7/1983 | Ehrnford |
| 4,431,451 A | 2/1984 | Mabie et al. |
| 4,631,793 A | 12/1986 | Shintaku et al. |
| 4,707,504 A | 11/1987 | Walkowiak et al. |
| 4,718,910 A | 1/1988 | Draenert |
| 4,735,625 A | 4/1988 | Davidson |
| 4,963,151 A | 10/1990 | Ducheyne et al. |
| 5,334,625 A | 8/1994 | Ibsen |
| 5,621,035 A * | 4/1997 | Lyles et al. .......... 433/226 |
| 6,291,547 B1 * | 9/2001 | Lyles et al. .......... 424/423 |

OTHER PUBLICATIONS

Gee, et al Jan. 1993 True linear polymerization shrinkage of unfilled resins and composites determined with a linometer; Dent Matar 9:11–14, pp. 11–14.

Feilzer, et al Jan. 1993 Setting stresses in composites for two different curing modes; Dent Mater 9:2–5, pp. 2–5.

Hosoda, et al Dec. 1990 SEM and elemental analysis of composite resins; The Journal of Prosthetic Dentistry, vol. 64 No. 6, pp. 669–676.

(List continued on next page.)

*Primary Examiner*—C. Melissa Koslow
(74) *Attorney, Agent, or Firm*—Baker Botts L.L.P.

(57) ABSTRACT

The preferred embodiment of the present invention provides novel and unique fused fibrous compounds for addition to and manufacture of bone and dental cement systems and methods of making the same. The preferred embodiment of the fused fibrous compound material made therefrom comprises a rigid three-dimensional network of fibers fused together at their points of contact wherein said network is greater than 60% by volume void space, has mean pore diameters greater than 10 microns, or both. The fused fibrous compound is preferably manufactured from fibers and a fusion source and is added to the composition in particle form.

26 Claims, 3 Drawing Sheets

OTHER PUBLICATIONS

Marshall, et al Oct. 1988 Restorative Dental Materials: Scanning electron Microscopy and Xray Microanalysis; Scanning Microscopy, vol. 2, No. 4, pp. 2007–2028.

Johnson, et al Aug. 1971 Effects of various finishing devices on resin surfaces; JADA, vol. 83, Aug. 1971, pp. 321–331.

Jaarda, et al Apr. 1993 Measurement of composite resin filler particles by using scanning electron microscopy and digital imaging; The Journal of Prosthetic Dentistry, vol. 69, No. 4, pp. 416–424.

Bowen & Antonucci Jan. 1976 Dimethacrylate Monomers of Aromatic Diethers; Journal of Dental Resins May–Jun. pp. 599–604.

Kilfoil, et al Jul. 1983 The tensile strength of a composite resin reinforced with carbon fibers; The Journal of Prosthetic Dentistry vol. 50, No. 1, pp. 40–43.

Hadavi, et al no date Resin/Amalgam Bond Strength; Assessing Microleakage (Operative Dentistry).

Neo, et al Dec. 1986 Effects of polymerization techniques of uniformity of cure of large–diameter, composite restorations; JADA, vol. 113, pp. 905–909.

Bowen Feb. 1967 Adhesive bonding of various materials to hard tooth tissues; JADA vol. 74, pp. 439–445.

Asmussen Jan. 1975 NMR–analysis of monomers in restorative resins; Acta Odont. Scand. 33, 129–134.

Brauer, et al 1979 no month Effect of Diluent on the Properties of Bis–GMA Based Composites; IADR Abstracts 1979, p. 243.

Antonucci Bowen Jul. 1975 Dimethacrylates Derived From Hydroxybenzoic Acids; J Dent Res Jan.–Feb. pp. 8–15.

Caldwell, et al Oct. 1957 Michrohardness studies of intact surface enamel; J. Dent. Res., pp. 732–738.

Ryge, et al Dec. 1961 Micro–identation Hardness; J. D. Res., vol. 40, No. 6, pp. 1116–1126.

Atmadja 1990 no month Some factors influencing the depth of cure of visible light–activated composite resins; Australian Dental Journal 1990;35(3):213–18.

Braem, et al Nov. 1985 The impact of Composite Structure on Its Elastic Response; J. Dent. Res., vol. 65, No. 5, pp. 648–653.

Nakayama et al Nov. 1973 Elastic properties of dental resin restorative materials;Journal of Dent Res, Sep.–Oct., vol. 53, No. 5.

Fan, et al Nov. 1979 In vitro wear of microfilled and visible light–cured composites; J. Dent Res, Nov., vol. 58, No. 11.

Mitchem Gronas Dec. 1985 The continued in vivo evaluation of the wear of restorative resins; JADA Research Reports, vol. 111, Dec. pp. 961–964.

Craig Apr. 1981 Chemistry, Composition, and Properties of Composite Resins; Dental Clinics of North America–vol. 25, No. 2.

Leinfelder Apr. 1981 Composite resins in posterior teeth; Dental Clinics of North America—vol. 25, No. 2 pp. 357–364.

Willems et al Sep. 1991 The surface roughness of enamel–to–enamel contact areas scared with the intrinsic roughness of dental composites; J Dent Res, Sep. vol. 70, No. 9, pp. 1299–1305.

Fan Powers Dec. 1980 In vitro wear of aged composite restorative materials; J Dent Res, vol. 59, No. 12, pp. 2066–2070.

Hosoda Dec. 1990 EM and elemental analysis of composite resins; Journal of Prosthetic Dentistry, vol. 64, No. 6, pp. 669–676.

Bowen & Marjenhof Sep. 1992 Dental Composites/Glass Ionomers: The Material; Adv Dent Res 6: 44–49.

Willems et al Sep. 1992 A classification of dental composites according to their morphological and mechanical characteristics; Dent Mater 8:310–319.

Jun. 1977 New American Dental Association Specification No. 27 for Direct Filling Resins; Reports of Councels and Bureaus/JADA, vol. 94, p. 1191–1194.

Leinfelder Apr. 1985 Composite Resins; Dental Clinics of North America—vol. 29, No. 2, pp. 359–371.

Lutz Phillips Oct. 1983 A classification and evaluation of composite resin systems; Fixed Prosthodontics/Operative Dentistry, vol. 50, No. 4, pp. 480–488.

Lambrech Vanherle 1983 Structural evidences of the microfilled composites; vol. 17, 249–260.

Craig May 1979 Selected Properties of Dental Composites; J Dent Res, vol. 58, No. 5, pp. 1544–1550.

Braem, Finger Sep. 1989 Mechanical properties and filler fraction of dental composites; Dent Mater 5:346–349.

Ameye, Lambrech 1981 Conventional and microfilled composite resins. Part I: Color stability and marginal adaptation; Journal of Prosthetid Dentistry, vol. 46, No. 6, pp. 623–630.

Robinson McCabe Nov. 1993 Impact strength of acrylic resin senture base materials with surface defects; Dental Materials 9:355–360.

Bowen Jan. 1963 Properties of a silica–reinforced polymer for dental restorations; Journal of the American Dental Association, vol. 66, pp. 57–64.

Bowen Oct. 1964 Effect of particle shape and size distribution in a reinforced polymer; Journal of the American Dental Association, vol. 69, pp. 481–495.

Mabie Menis 1978 no month Microporous Glassy Fillers for Dental Composites; Journal of Biomedical Materials Research, vol. 12, 435–472.

Söderhol Nov. 1981 Degradation of Glass Filler in Experimental Composites; J Dent Res 60(11):1867–1875.

Ruyter Aug. 1988 Composites–Characterization of composite filling materials: Reactor Response; Adv Dent Res 2(1):122–129.

Leinfelde Aug. 1988 Current Developments in Posterior Composite Resins; Adv Dent Res 2(1):115–121.

Raptis, Fan, Pow Oct. 1979 Properties of microfilled and visible light–cured composite resins; JADA, vol. 99, pp. 631–633.

Lacy Mar. 1987 A critical look at posterior composite restorations; JADA, vol. 114, pp. 357–362.

Hinoura Moore Feb. 1987 Tensile bond strength between glass ionomer cements and composite resins; JADA, vol. 114, pp. 167–172.

Dennison Craig Jul. 1972 Physical properties and finished surface texture of composite restorative resins; JADA, vol. 85, pp. 101–108.

Asmussen 1985 no month Clinical Relevance of Physical, Chemical, and Bonding Properties of Composite Resins; Operative Dentistry, vol. 10, pp. 61–73.

Davidson Gee Feb. 1984 Relaxation of Polymerization Contraction Stresses by Flow in Dental Composites; J Dent Res 63(2):146–148.

Stanford Fan Nov. 1987 Radiopacity of light–cured posterior composite resins; JADA, vol. 115, pp. 722–724.

Fan, Edahl Jan. 1985 Alternative Interpretations of Water Sorption Values of Composite Resins; J Dent Res 64(1):78–80.

Dennison Powers Apr. 1978 Color of Dental Restorative Resins; J Dent Res 57(4):557–562.

Ferracane Moser Sep. 1981 Rheology of Composite Restoratives; J Dent Res 60(9):1678–1685.

Hirasawa Hirano Jan. 1983 Initial Dimensional Change of Composite in Dry and Wet Conditions; J Dent Res 62(1):28–31.

Oysaed Ruyter Nov. 1986 Water Sorption and Filler Characteristics of Composites for Use in Posterior Teeth; J Dent Res 65(11):1315–1318.

Powers Hostetler Feb. 1979 Thermal expansion of composite resins and Sealants; J Dent Res 58(2):584–587.

Braden Aug. 1988 Some aspects of the chemistry and physics of dental resins; Adv Dent Res 2(1):93–97.

Vallittu no date A review of reinforcing the polymethyl methacrylate with metal strengtheners; pp. 1–40 plus figures.

Goldberg and Burstone May 1992 The use of continuous fiber reinforcement in dentistry; Dent Mater 8:197–202.

Ehrnford Oct. 1981 Composite resins with a condensable inorganic phase; J Dent Res 60(10):1759–1766.

Ehrnford 1976 no month A method for reinforcing dental composite restorative materials; Odont. Revy 27:51–54.

Cross Douglas Jul. 1983 The relationship between filler loading and particle size distribution in composite resin technology; J Dent Res 62(7):850–852.

Ehrnford 1984 no month Surface characteristics of composite resins comprising a porous reinforcing filler; Acta Odontol Scand 42 pp. 59–64.

Latour Black 1992 no month Develpoment of FRP composite structural biomaterials: Ultimate strength of the fiber/matrix interfacial bond in in vivo simulated environments; Journal of Biomedical Materials Research, vol. 26, 593–606.

Skirvin Vermilyea Dec. 1982 Polymethylmethacrylate Reinforcement: Effect on fatigue failure; Military Medicine, vol. 147, pp. 1037–1040.

Grave Chandler Jun. 1985 Denture base acrylic reinforced with high modulus fibre; Dent Mater 1985:1: 185–187.

Ruffino 1985 no month Effect of steel strengtheners on fracture resistance of the acrylic resin complete denture base; Journal of Prosthetic Dentistry, vol. 54, No. 1, p. 75–77.

Schreiber Jan., 1971 Polymethylmethacrylate Reinforced with Carbon Fibres; Brit Dent J 1971, 130, 29–30.

Gutteridg 1992 no month Reinforcement of poly(methylmethacrylate) with ultra–high–modulus polyethylene fibre; J. Dent. 1992; 20: 50–54.

Braden 1988 no month Denture base poly(methyl methacrylate) reinforced woth ultra–high modulus polyethylene fibres; Br. Dent. J. 1988; 164:109–112.

Andreopo Papaspyri Jan. 1991 Surface treated polyethylene fibres as reinforcement for acrylic resins; Biomaterials, vol. 12, pp. 83–87.

Gutteridg 1988 no month The effect of including ultra–high–modulus polyethylene fibre on the impact strength of acrylic resin; British Dental Journal 1988; 164: 177, pp. 177–180.

Björk Ruyter 1986 no month Implant–fixed, dental bridges from carbon/graphite fibre reinforced poly (methyl methacrylate); Biomaterials 1986, vol. 7 Jan., pp. 73–75.

O'Brien 1989 no month Dental Materials: Properties and Selection; Quintessence Publishing Co., Inc. 1989, pp. 157–170.

Ruyter Ekstrand 1985 no month Development of carbon/graphite fiber reinforced poly(methyl methacrylate) suitable for implant–fixed dental bridges; Dent Mater 1986: 2; 6–9.

Malquati Berruet 1990 no month Prosthetic use of carbon fiber–reinforced epoxy resin for esthetic crowns and fixed partial denures; J Prosthet Dent 1990; 63: 251–7.

Markus 1994 no month An indirect/direct combined approach for a reinforced fixed bridge; Journal of the New Jersey Dental Association/Winter 1994, pp. 23–26.

Nov. 1993 Product Spotlight—GlasSpan Flexible Ceramic Bonded Reinforcement Material—The Indirect GlasSpan Bridge; Trends & Techniques; Nov. 1993, pp. 24–25.

Altieri Burstone Jan. 1994 Longitudinal clinical evaluation of fiber–reinforced composite fixed partial dentures: A pilot study; Prosthet Dent 1994; 71:16–22.

Burgess Mar. 1993 Flexural Strength of five Provisional Materials; IADR General Session and Exhibition, Seattle Washington.

Andreopo Petsalas 1992 no month Reinforcement of acrylic polymers with rediopaque cellulose fibres; Journal of material Science; 27: 734–36.

Willems Lambrech 1993 no month Composite resins in the 21st century; Quintessence International vol. 24, No. 9, pp. 641–657.

Albers 1991 no month ADEPT Report; vol. 2, No. 4. pp. 53–64.

Farah 1991 no month Anterior and Posterior Composites; The Dental Advisor; 1–8.

Knoell, et al 1975 no month Graphite Fiber Reinforced Bone Cement, Ann. Biomed. Eng. 3, pp. 225–229.

Pilliar et al 1976 no month Carbon Fiber–Reinforced Bone Cement in Orthopedic Surgery, J. Biomed. Mater. Res., vol. 10., 1976, pp. 893–906.

Reifsnider 1977 no month Fatigue of Filamentary Component Materials, ASTM STP 636, ASTM, pp. 206–227.

Wright et al. 1979 no month Mechanical Properties of Aramid Fibre–Reinforced Acrylic Bone Cement, J. Mater. Sci. Let., 14, pp. 503–505.

Beaumont 1977 no month J. Mater. Sci., 12, pp. 1845–1852.

Taitsman, Saha Apr. 1977 J. Bone. Joint Surg., vol. 59–A, No. 3, pp. 419–425.

Fishbane Pond 1977 no month Stainless Steel Fiber Reinforcement of Polymethylmethacrylate, Clin. Orthop., No. 128, pp. 194–199.

Schnur, Lee 1983 no month Stiffness and inelastic deformation in acrylic–titanium composite implant materials under compression, J. Biomed. Mater. Res., vol. 17, pp. 973–991.

Robinson, et al 1981 no month J. Biomed. Mater. Res., vol. 15, pp. 203–205.

Saha, Pal 1984 no month Improvement of mechanical properties of acrylic bone cement by fiber reinforcement, J. Biomechanics, vol. 17, No. 7, pp. 467–478.

Ekstrand 1987 no month J. Biomed. Mater. Res., vol. 21, pp. 1065–1080.

Pourdeyhi mi, et al 1986 no month Ann. Biomed. Eng., 14, pp. 277–294.

Pilliar et al. 1977 no month Mechanical Properties of Carbon–fiber Reinforced Polymethylmethacrylate for Surgical Implant Applications, Fatigue of Filamentary Composite Materials, pp. 206–227.

* cited by examiner

BONE CEMENT COMPOSITIONS COMPRISING FUSED FIBROUS COMPOUNDS

FIELD OF THE INVENTION

This application is a continuation patent application of U.S. patent application Ser. No. 09/174,753, filed Oct. 19, 1998, now issued as U.S. Pat. No. 6,291,547 on Sep. 18, 2001, which is a continuation of U.S. patent application Ser. No. 08/684,251, filed on Jul. 19, 1996, now abandoned, which was a continuation-in-part of U.S. patent application Ser. No. 08/386,305, filed Feb. 8, 1995, now issued as U.S. Pat. No. 5,621,035.

The invention is directed to improved bone cement and dental cement systems comprising fused fibrous compounds and methods of making the same. The invention is further directed to bone cement and dental cement system kits for bone or teeth repair or other treatment of bone and teeth.

BACKGROUND OF THE INVENTION

In joint surgery it is common practice today to anchor components of replacement joints by using as bone cement a two-component resin which polymerizes during the operation at normal temperatures and which, on account of its plastic properties leads to an interlocking of the prosthesis component in the bony sheath. Because of its physical properties, the bone cement shrinks onto the prosthesis resulting in a closed metal-tocement contact.

The bone cements commonly used are polymethylmethacrylate (PMMA) consisting of powdery bead polymers which are superficially dissolved by liquid monomers and embedded during the polymerization process. During mixing the polymer is immersed in the monomers. The PMMA beads are superficially dissolved and embedded in a composite manner. Despite their widespread use PMMA and related bone cements tend to represent the "weak link" in prosthesis fixation.

The long term success of a total joint prosthesis depends on the continued function and interaction of each of the components of the prosthetic system. In a cemented total hip prosthesis, for instance, stress transfer from the pelvis to the femur is a function of the materials between the two bones (e.g. bone-PMMA-metal-Ultra-high Molecular Weight Polyethylene-metal-PMMA-bone) and the interfaces between the materials. The weakest of the materials is the PMMA, with the lowest fracture toughness and ultimate strength.

The common mode of failure of total joint prostheses is aseptic loosening. X-ray Aexaminations of patients with loosened prostheses often reveal a radiolucent line in the bulk of the cement, indicating that the cement has fractured. Because the geometry of the prosthesis is complex, the state of stress is also highly complex, and the reasons for cement failure are not clear. For example, it has been postulated that the integrity of the metal stem/PMMA interface is the critical link in the performance of the prosthesis; however, the cause and effect relationship between the metal prosthesis/PMMA interface failure and cement fracture is not well understood although the fracture mechanics of the two phenomena are most likely linked. The improvement of the fracture characteristics of the bone cement, however, is a problem that has received some attention in recent years.

The composition of the PMMA used for total joint surgeries today is substantially the same as that used 20 years ago; very little has been done to improve the material itself.

The acceptable success rate of cemented prostheses was achieved using existing cements, however, in a predominantly elderly patient population and with improved surgical handling techniques. The 90% success rate at ten years is good, but should be improved. Cement failures do occur, and generally lead to revision surgery. Furthermore, younger patients now receiving total joint replacements have a greater life expectancy than the design expectations of the total joint prosthesis. Improvement of the bone cement, exclusively, may not solve every problem associated with total joint replacements. But, by making improvements in each component of a total joint prosthesis, including the cement, the success rate of prostheses will improve, and mechanical failures can be virtually eliminated.

Increasing the longevity of PMMA by improving the resistance to failure of the polymer has received some, albeit surprisingly little, attention in the bioengineering literature in the past ten years. One suggested method of improvement was to formulate a new bone cement, based on n-butyl methacrylate, rather than the methyl methacrylate monomer. It has been reported that the material showed a higher ductility, a higher apparent fracture toughness, and a greater fatigue life. However, the actual fracture toughness determined by separate impact tests showed no improvement of the newn cement with respect to PMMA cements. An even more detrimental result was that the new polymer had only half the modulus and half the ultimate tensile strength of PMMA.

Another method of attempting to improve PMMA was the addition of a reinforcing phase, generally short fibers or whiskers. Early work was done by Knoell, et al., Ann. Biomed, Eng., 3, 1975, pp. 225–229 with carbon fibers approximately 6 mm in length, 1, 2, 3 and 10% fiber content by weight (approximately 0.67, 1.33, 1.96 and 5.87% fiber content by volume, with measured increases of 100% in the average Young's modulus for the reinforced PMMA. They also reported a decrease in peak curing temperature of the reinforced PMMA. They found the reinforced cement viscous and difficult to mix, and they altered the ratio of powder polymer to liquid monomer to facilitate mixing of the reinforced cement. Pilliar, et al.,J. Biomed. Mater. Res., Vol. 10, 1976, pp. 893–906); Fatigue of Filamentary Component Materials ASTM STP 636, eds. Reifsnider, et al., ASTM 1977, pp. 206–227; used carbon fibers (6 mm length, 7 micrometers diameter) with a 2% volume content. They measured a 50% improvement in tension-tension fatigue limit, improved impact performance, and a 36% increase in ultimate tensile strength. However, it was implied that the reinforced PMMA had poor intrusion characteristics due to increased viscosity, and poor fiber distribution. Wright, et al. J. Mater. Sci. Let., 14 1979, pp. 503–505, did preliminary studies using PMMA reinforced with chopped aramid fibers. PMMA reinforced with 5.17% by volume (7% by weight) exhibited a 74% increase in fracture toughness over the plain PMMA. They were not able to produce reinforced PMMA with a fiber content greater than 5% by volume because of mixing and handling difficulties. Beaumont, J. Mater. Sci., 12, 1977, pp. 1845–1852 included glass beads in the PMMA mass and measured a $10^3$ decrease in crack propagation velocity, using 30% volume content of the beads.

Very few investigations involved the use of metal fibers to reinforce PMMA. Taitsman and Saha, J. Bone Joint Sizug., Vol. 59-A, No. 3, Apr 1977, pp. 419–425, used large diameter (0.5 to 1.0 mm) stainless steel and vitallium wires as a reinforcing phase. They embedded 1, 2, or 3 wires in their PMMA specimens. They reported up to an 80% increase in tensile strength of the PMMA, with three embedded vitallium wires, but noted that clinical applications of their wire reinforced cement were limited. Taitsman and Saha's use of reinforcing wires is analogous to reinforcing bars embedded in structural concrete, and not a homogeneous, fiber composite material. Fishbane and Pond, *Clin. Orthop.*, No. 128, 1977, pp. 194–199, reinforced industrial grade PMMA and PMMA bone cement with stainless steel whiskers (0.5–1.0 mm length and 65 micron diameter; 3–6 mm length and 90 microns diameter). They determined that the addition of fibers up to 6.5% by volume improved the compressive strength by nearly 100% for the industrial PMMA, but only 25% for the surgical grade PMMA. The compressive strength of PMMA is not a critical property for the longevity of the cement in vivo. These authors postulate that the reason for the decreased performance of the surgical PMMA was: "... due to the limitations imposed by the (surgical) methacrylate preparation technique."

Schnur and Lee, *J. Biomed. Mater. Res.*, Vol. 17, 1983, pp. 973–991, used titanium (Ti) sheet, wire, mesh and powder as a reinforcing phase with the purpose of increasing the modulus of PMMA to the modulus of cortical bone. A 16% volume fraction of 1 mm diameter wires (a total of 25 wires) increased the modulus of the PMMA by 380%, and the maximum compressive stress by 75%. The concept is again similar to the reinforcing bars embedded in concrete.

The more recent work in reinforcing PMMA bone cement as reported in the literature, has involved either carbon, graphite, or aramid fibers. Robinson, et al., *J. Biomed. Mater. Res.*, Vol. 15, 1981, pp. 203–205, tested both regular PMMA and low viscosity PMMA cement (available from Zimmer Co., Warsaw, Ind.) reinforced with 2% volume of carbon fibers (1.5 mm in length, 10 microns diameter). Both reinforced cements exhibited an increase in apparent fracture toughness (notched bending strength tests) of approximately 32% over their plain counterparts. Surface fractography revealed no evidence of fiber fracture, indicating that the increases in "toughness" was due principally to fiber pull out. In other work with carbon fiber reinforced PMMA an order of magnitude decrease in crack propagation velocity was attributed to the carbon fiber reinforcement of both the regular and low viscosity cements.

Salia and Pal, *J. Biomechanics*, Vol. 17, No. 7, 1984, pp. 467–478, tested PMMA reinforced with carbon fibers, 0.67% by volume (1% by weight; 6 mm length, 8 microns diameter) and PMMA reinforced with aramid fibers (Dupont Kevlar-29), 1.61 and 3.82% by volume (2 and 4% by weight; 12–13 mm length, unspecified diameter). The reinforced PMMA showed an increase in the ultimate compressive strength of 20.5% for the carbon fibers, and 19.5% and 28.7% for the 1.61 and 3.82% volume % aramid fibers, respectively. Two important consequences of the addition of fibers to PMMA were proposed: The peak temperature of the reinforced PMMA was lower than the plain PMMA, and the addition of fibers changed the workability of the cement. They recognized that uniform dispersion of fibers was not achieved. Saha and Pal studied a machine mixing technique for distributing the fibers. Their claim that machine mixed specimens were stronger than non-machine mixed specimens is misleading. They used a different shaped fiber for their machine mixed specimens. It is the superior shape of the fiber which is presumed to account for the increase in strength. Machine mixing was never shown to improve the properties of reinforced PMMA.

Ekstrand, *J. Biomed. Mater. Res.*, Vol. 21, 1987, pp. 1065–1080, fabricated carbon fiber reinforced PMMA by using clinically irrelevant, industrial fabrication techniques with fiber content as high as 16.38% by volume (40% by weight).

Recent work by Pourdeyhimi, et al., *Ann. Biomed. Eng.*, 14, 1986, pp. 277–294, studied the effect of the fiber content of the fracture toughness of hand-mixed, reinforced, dental PMMA. They used aramid fibers from 0.82 to 5.17% by volume (1 to 7% by weight), and graphite from 0.67 to 5.87% by volume (1 to 10% by weight). For each type of fiber reinforced cement, the fracture toughness increased with increased fiber content. The aramid fiber specimens showed a greater increase than the carbon fiber specimens of the same weight percent, presumably because the energy dissipated in the micromechanisms of failure is greater for the aramid fibers than for the carbon fibers. They were not able to produce a uniform distribution of the fibers.

U.S. Pat. No. 4,064,566 to Fletcher, et al. discloses a graphite fiber reinforced bone cement of the acrylic type stated to have mechanical properties more nearly matched to those of bone and thermal curing characteristics resulting in a lower exothermic temperature reaction during curing. The bone cement composition is a dispersion of from 2 to 12% by weight of very fine high modulus graphite fibers having a diameter below 50 microns and between 0.1 and 15 mm in average length in a solution of biocompatible polymer dissolved in a reactive monomer. Fletcher reports only an increase in the modulus of the bone cement, which may not be of primary concern to a reinforced bone cement, and indeed can be detrimental to the prosthesis system. There was a decrease in compressive strength, and more negatively, a decrease in flexural strength for the reported composite.

U.S. Pat. No. 4,239,113 to Gross, et al. discloses an acrylic based bone cement filled with between 15 and 75% by weight of inorganic material comprised of about 90 to 99% by weight of a bio-active glass ceramic powder and about 1 to 10% by weight of vitreous mineral, e.g., glass, fibers having a length below about 20 nm. The particle size of the powder is from 10 to 200 micrometers. Fiber diameters are not disclosed. Improvements in impact strength, and compression strength were reported. However, a significant decrease in the bending strength and an increase in the modulus of elasticity were also reported. Further, there are no examples given as to the clinical usefulness of this cement. Bioactive glass degrades with time, and hence the integrity of the reinforced bone cement will also degrade with time. The controlled experimentation shows that there is no mechanical improvement due to the fiber reinforcing phase alone. Any improvement is due to the combination of bioactive glass and fiber in concert. Since the bioactive glass degrades with time, the properties of the reinforced cement proposed by Gross, et al. will also degrade with time.

Davidson, in U.S. Pat. No. 4,735,625, reports the invention of a reinforced bone cement formed using a sock-like mesh of a fiber-like material to reinforce the cement in the vicinity of the prosthesis. The volume of "reinforced" bone cement is limited; critical areas are not reinforced. Draenert, in U.S. Pat. No. 4,365,357, presents an invention similar to Davidson's, but using a mesh of polymeric fibers. The invention is restricted to use in repairing bone defects, and not as a bone cement in the sense described for total joint arthroplasty. Draeneit, in U.S. Pat. No. 4,718,910, describes a bone cement mixture where a second phase of fibers is added. The fibers, however, are made up of the same polymeric material as the bone cement. Draenert includes a graph of the performance of the new material versus existing cements. The inventor states that the fiber is only effective because of the shape of the prepolymer powder. Therefore, the improvement is due to the use of a different cement, and not to the addition of the fibers.

Duclheyne et al. in U.S. Pat. No. 4,963,151 disclose the distribution of short, fine, reinforcing fibers homogeneously throughout surgical bone cement by adding the fibers in the form of bundles of several hundred fibers with the fibers bonded to each other with an adhesive binder that is soluble in the liquid monomer component of the bone cement.

It is generally agreed that as the quantity of reinforcing fibers increases so do the mechanical strength properties. However, as the fiber content increases it becomes increasingly difficult and eventually not practical or possible to effect homogeneous distribution of the fibers throughout the cement mass and in addition the viscosity of the mass increases and its workability by the surgeon during surgery decreases. Any practically useful surgical bone cement must be capable of being easily mixed by the surgeon in a clinical setting, i.e., during surgery, and must remain sufficiently flowable and workable to be applied to the bone surface or cavity and/or to the prosthesis or other implant device.

SUMMARY OF THE INVENTION

Accordingly, it is an object of the invention to provide a surgical bone dental cement with improved mechanical properties, including fracture toughness and fatigue strength, thereby improving long term prognosis of total joint replacements and other surgical bone repair treatments involving bone cements.

It is another object of the invention to provide a fused fibrous reinforced surgical bone dental cement wherein mixing of the fiber reinforcement into the cement matrix can be easily performed by the surgeon under clinical conditions.

Still other objects of the invention are to provide a novel fused fibrous reinforcing material which can be easily and homogeneously incorporated into a two component bone or tooth cement including biocompatible polymer beads or powder and biocompatible reactive liquid monomers; a bone dental cement treatment kit for surgical bone/tooth repair which kit includes the fused fibrous material, biocompatible polymer and reactive liquid monomer; and a method for uniformly and homogeneously incorporating fused fibrous material into a two component acrylic based surgical bone/dental cement.

The above and other objects of the invention which will become more apparent after reading the following detailed description and preferred embodiments in conjunction with the accompanying drawings are accomplished, according to a first aspect of the invention, by an acrylic based surgical bone cement with fused fibrous compound added thereto.

The fused fiber material can be provided as a component of a bone or tooth cement treatment kit for surgical bone/dental repair or other treatment of a bone/dental disease or bone/dental defect requiring application of a surgical bone/dental cement. The kit includes a biocompatible polymer, generally in the form of powder or beads, a liquid reactive monomer, and a plurality of fused fibrous compound particles wherein the fibers in each particle are fused to each other at their points of contact with a fusion source, said fusion point not soluble in the liquid reactive monomer.

The present invention, according to one embodiment, is directed to an improved bone cement composition comprising bone/dental cement, and a fused fibrous compound. According to another embodiment, the bone/dental cement composition may comprise polymethylmethacrylate, methylmethacrylate-styrene-copolymer, and a radiopacifier. According to further embodiment, the bone cement composition comprises barium sulfate.

According to some embodiments, the bone/dental cement compositions of the present invention may include fused fibrous compounds in the form of particles of different sizes, e.g., ranging from about 10 microns to about 1000 microns in diameter.

According to further embodiments, the bone/tooth cement compositions of the present invention may be comprised of fused fibrous compound of up to about 10%, 20%, 30%, 40%, 50%, 60% and/or 70% of the total weight of the composition.

According to another embodiment, the bone cement compositions of the present invention may comprise fused fibrous compounds having at least about 60% by volume void space and/or mean pore diameters of greater than about 10 microns. Preferably, the compound of the present invention comprises 88% by volume void space. Probably, the bone/teeth cement compositions of the present invention include fused fibrous compounds which are silanated.

According to a still further embodiment of the present invention, the bone/dental cement compositions of the present invention may include fused fibrous compounds manufactured from alumina fibers, silica fibers and a fusion source, e.g., boron nitride. Preferably, the bone/dental cement compositions of the present invention include fused fibrous compounds comprising about 21% by weight alumina and about 74% by weight of the fused fibrous compound. Preferably, the bone/dental cement compositions of the present invention include fused fibrous compounds made from alumina fibers having an average diameter of from about 1 to about 100 microns and silica fibers having an average diameter of from about 1 to about 6 microns.

The present invention is also, according to a further embodiment, directed to methods for improving bone/dental cement compositions comprising adding fused fibrous compounds (e.g., those described above) to bone/dental cement compositions.

A bone/dental cement treatment kit for bone repair or other treatment of a bone/dental defect, said kit comprising: (1) finely divided acrylic polymer, (2) polymerizable liquid acrylic monomers for preparation of bone/dental cement useful in bone/tooth repair or other bone/tooth treatment, and (3) a fused fibrous compound.

DESCRIPTION OF THE PREFERRED EMBODIMENTS

Figure 1:
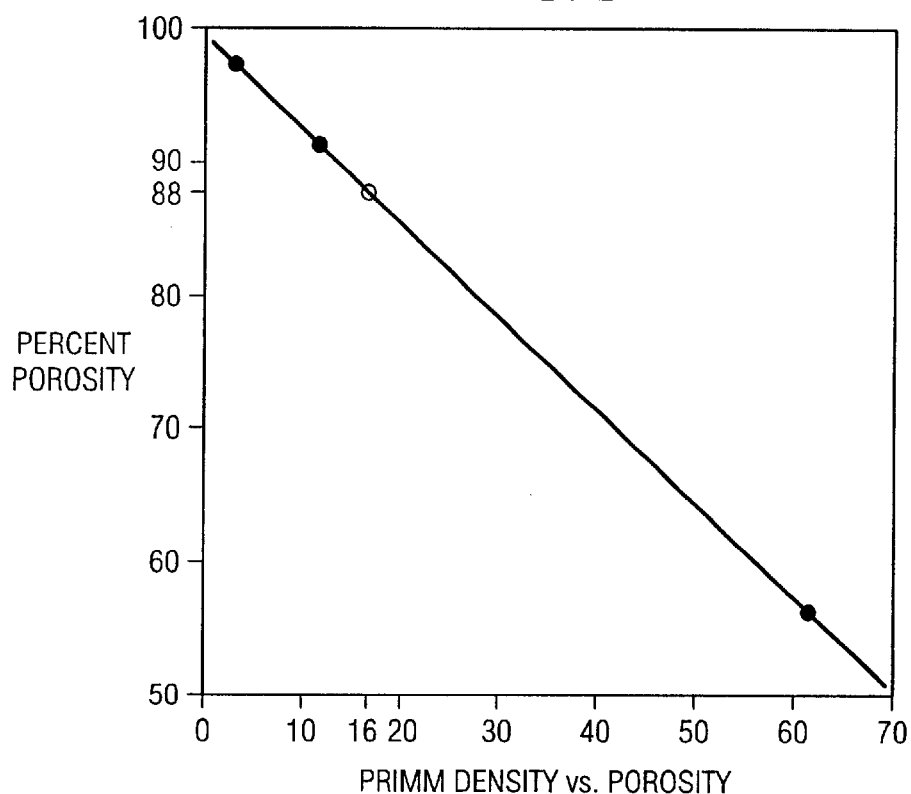
FIG. 1 is a plot or graph of the density versus the porosity of the fused fibrous compound of the present invention.

In this invention, the terms "(meth)acrylate" and "poly (meth)acrylate" include the monomers and polymers, respectively, of methacrylic acid esters and acrylic acid esters, and the polymers also include the co-polymers of the compounds named.

The preferred bone cement material to which the fused fibrous compound is added includes a solid finely divided powdery or granular polymer component and a liquid reactive or polymerizable monomer component which is also a solvent or swelling agent for the polymer component. The polymer and monomer components can be based on the acrylic, e.g., (meth)acrylate system, however, other polymeric systems can also be used. For convenience, the cement system may at times be broadly referred to as an acrylic polymer, or as based on PMMA (polymethylmethacrylate), the preferred polymer component. While the invention is described herein in terms of a preferred embodiment, i.e., bone cement, it is to be understood that the invention is also directed to dental/tooth cements.

More generally, the polymer component of the composition can be any methyl(meth)acrylate polymer such as methyl(meth)acrylate homopolymers and copolymers of methyl(meth)acrylate with alpha, beta-ethylenically unsaturated compounds such as vinyl acetate, alkyl (e.g., $C_2$–$C_6$) (meth)acrylates and multi-functional acrylic monomers such as alkylene dimethacrylate and alkylene diacrylates and triacrylates. These polymers generally have a molecular weight between 500,000 and 2,000,000. Methylmethacrylate homopolymers and copolymers are preferred.

The reactive monomer component is preferably methyl acrylate or methyl methacrylate although the $C_2$–$C_4$ alkyl (meth)acrylates, such as ethyl(meth)acrylate, propyl(meth) acrylate or (n-, or iso-)butyl(meth)acrylate, can also be used.

These bone cement materials, which are themselves wellknown and commercially available, are usually provided with 2 parts by weight of the finely divided polymer and 1 part by weight of liquid monomer, although higher or lower ratios can also be used, and are characterized as being self-polymerizable substances which are mixed, together with a polymerization catalyst, such as dibenzoyl peroxide, and polymerization accelerator, such as dimethyl-p-toluidine, immediately prior to the operation to form a viscous liquid or pasty mass. The pasty mass is introduced into the appropriate body cavity and/or to the surgical implant, device, and will harden in situ, at room temperature (via an exothermic reaction) within a few minutes.

More specifically, curing of bone cement composition is typically accomplished by any suitable initiator system such as from about 0.1 to about 3% by weight, preferably about 0.6% of a conventional free radical initiator. The initiator can be a peroxy compound or an azo compound. For purposes of biocompatability benzoyl peroxide is a very suitable free radical initiator. The curing temperature is generally reduced to room temperature, e.g. about 25° to 30° C., by inclusion in the formulation of an activator for the peroxide catalyst which causes more rapid decomposition of the peroxide to form free radicals. Suitable peroxide catalysts include benzoyl peroxide, 2,4-dichlorobenzoyl peroxide and 4-chlorobenzoyl peroxide. Activators or accelerators for these catalysts include N,N-dialkyl anilines or N,N-dialkyl toluidines generally employed in amounts ranging from about 0.1 to 1% based on the weight of monomer present. A preferred activator is N,N-di(2-hydroxyethyl)-p-toluidine. In order to provide longer shelf life for the compositions of the invention, the composition may be stored in a closed container at cold temperature. Stabilizers, such as hydroquimone or chlorophyll may also be added to the monomer compound. Bone cements containing both activator and peroxide are provided as two-part compositions in which the activator and monomer and peroxide and polymer component are packaged in separate containers. The proportions by weight of polymer and liquid monomer can range from about 4:1 to 1:2, preferably 3:1 to 1:1.5, such as 2:1, 1.5:1, 1:1 or 1:1.5.

Generally, the fused fibrous compound component of the present invention has been described above in the Summary Of The Invention. However, several fused fibrous compound compositions falling within the description set forth above are particularly preferred. Generally, the fused fibrous compound materials of the present invention are manufactured utilizing alumina fibers, silica fibers, and from about 1% to about 5% boron, preferably boron nitride.

One preferred embodiment of the fused fibrous compound material of the present invention is comprised or manufactured from of about 1% to about 50% by weight alumina, from about 50% by weight to about 98% by weight silica, and boron. Another preferred embodiment of the fused fibrous compound material is manufactured utilizing: (1) from about 15% to about 30% by weight alumina fiber; (2) from about 65% to about 85% by weight silica fiber; (3) from about 1% to about 3% by weight silicon carbide; and (4) from about 1% to about 5% by weight boron nitride.

Another more preferred fused fibrous compound material of the present invention is manufactured from: (1) about 21% by weight alumina fiber; (2) about 74% by weight silica fiber; (3) about 2% by weight silicon carbide; and (4) about 2.85% by weight boron nitride. Preferably, the material of the present invention is manufactured utilizing alumina and silica fibers in a ratio of 22:78 by weight. For strength, a preferred ratio of alumina to silica is 30:70 by weight.

Moreover, a preferred embodiment of the fused fibrous compound material of the present invention comprises: a rigid three-dimensional network of inorganic or organic fibers fused together at their points of contact wherein said network has mean pore diameters of greater than about 10 microns, or has greater than about 60% by volume void space, or both. The fused fibrous compound may be, in some embodiments, in the form of particles or branched fibers.

The fused fibrous compound materials of the present invention have many advantageous properties needed for bone cement applications. The fused fibrous compound material of the present invention has exceptional physical, chemical, and mechanical properties which are imparted to varying degrees depending upon the application to bone cements manufactured utilizing the material, these properties include, inter alia: (1) low to high density—4 lb./ft.$^3$ to 62 lb./ft.$^3$; (2) low thermal conductivity—e.g., for 12 lb./ft.$^3$ density at 500° F. conductivity=0.61 Btu—in./ft.$^2$; (3) purity—predominately comprised of 99.7% pure silica fibers and 95.2% pure alumina fibers; (4) long life in cyclic applications—e.g., 12 lb./ft.$^3$ density, does not degrade with cyclic exposure to 2600° F. and can even withstand limited exposure to 2900° F.; (5) rigidity—maintains shape and supports mechanical loads while providing thermal insulation (i.e., has a high compressive strength and tensile strength (MN/m2) (6) high flexural strength—modulus of rupture for 4 lb./ft.$^3$ to 62 lb./ft.$^3$ densities ranges from 100–6200 lb./in.$^2$; (7) inert—does not burn, softens at temperatures above 2700° F. and melts at about 3100° F.; (8) dimensional stability—has a low coefficient of thermal expansion and 0.4% linear shrinkage; (9) thermal shock resistance—can be heated to 2600° F. and immediately immersed in cold water without damage; (10) high diffusivity—12 lb./ft.$^3$ to 62 lb./ft.$^3$ ranges from 97% to 56%;

(11) porosity—highly porous (over 60% by volume void space, preferably between about 60% and about 98% by volume void space, most preferably over 80% by volume void space) and offers minimal resistance to the passage of gases or liquids (mean pore diameters greater than 10 microns, generally between 10 and 25 microns, most preferably from about 20 to about 22 microns); (12) able to coat or bond to other materials (i.e., materials, plastics, metals, inorganics) with relative ease to enhance characteristics. In addition, the 16 lb/ft$^3$ density filler material of the present invention has (1) a flexural modulus of strength—$2.5 \times 10^{10}$ Pa, (2) a Rockwell Hardness—50, (3) Surface Roughness of 0.6 Ra, and (4) linear shrinkage of 0.4% after repeated cycles at temperatures above 2700° F. As a result, e.g., the bone cements made with the fused fibrous compound material of the present invention have heretofore unknown improved linear shrinkage, flexural strength, and flexural modules.

Generally, the process for the manufacture of low density, like 16 lb. per ft.$^3$, fused fibrous compound material (discussed in terms of a preferred alumina/silica embodiment) is comprised of the following steps:

(1) preparation of a slurry mixture comprised of pre-measured amounts of purified fibers/materials and deionized water;

(2) removal of shot from slurry mixture;

(3) removal of water after thorough mixing to form a soft billet;

(4) addition of a ceramic binder after the formation of the billet;

(5) placement of the billet in a drying microwave oven for moisture removal; and (6) sintering the dry billet in a large furnace at about 1600° F. or above.

High purity silica fibers are first washed and dispersed in hydrochloric acid and/or deionized water or other solvents. The ratio of washing solution to fiber is between 30 to 150 parts liquid (pH 3 to 4) to 1 part fiber. Washing for 2 to 4 hours generally removes the surface chemical contamination and non-fibrous material (shot) which contributes to silica fiber devitrification. After washing, the fibers are rinsed 3 times at approximately the same liquid to fiber ratio for 10 to 15 minutes with deionized water. The pH is then about 6. Excess water is drained off leaving a ratio of 5 to 10 parts water to 1 part fiber. During this wash and all following procedures, great care must be taken to avoid contaminating the silica fibers. The use of polyethylene or stainless steel utensils and deionized water aids in avoiding such contamination. The washing procedure has little effect on the bulk chemical composition of the fiber. Its major function is the conditioning and dispersing of the silica fibers.

The alumina fibers are prepared by dispersing them in deionized water. They can be dispersed by mixing 10 to 40 parts water with 1 part fiber in a V-blender for 2½ to 5 minutes. The time required is a function of the fiber length and diameter. In general, the larger the fiber, the more time required.

Generally, in order to manufacture ultra-low density fused fibrous ceramic filler material, for example, densities below 12 lb./ft.$^3$, the process includes the additional steps of:

(1) the addition of expendable carbon fibers in the casting process and/or other temporary support material; and (2) firing the billet at about 1300° F. to remove the carbon fibers or other support material prior to the final firing at approximately 1600° F. or above.

When the dispersed silica fibers and dispersed alumina fibers are combined, the pH is probably acidic and should be adjusted to neutral with ammonium hydroxide. The slurry should contain about 12 to about 25 parts water to about 1 part fiber. The slurry is mixed to a uniform consistency in a V-blender in 5 to 20 minutes. The boron nitride can be added at this point (2.85% by weight of the fibers) and mixed to a uniform consistency in a V-blender for an additional 5 to 15 minutes creating a Master Slurry. The preferred mixing procedure uses 15 parts water to 1 part fiber and the slurry is produced in about 20 minutes of mixing. At lower density formulations, expendable carbon fibers are used to give "green" strength to the billet prior to the final sintering. The percent of carbon fiber used varies greatly depending on the diameter, length and source of the fiber and the ultimate density of the material being produced. The percent of carbon fiber per dry weight of material should range between 1 and 10%. The source of the carbon fiber can take many forms including nylon, cellulose, and purified graphite based carbon in fibrous form. Carbon fibers added in the casting process are eliminated by firing the billets at 1350° F. prior to the final firing at 2450° F.

The Master Slurry is poured into a mold for pressing into the desired shape. The water is withdrawn rapidly and the resulting felt is compressed at 10 to 20 psi. Rapid removal of the water is required to prevent the fibers from separating. If graded properties are desired in the resultant material, the slurry can be allowed to settle and the fibers to partially separate before the removal of the water.

The final density of the finished restorative material is determined in part by the amount of compression placed on the felt, varying the wet molded dimension in relation to the fiber content. The formulation of the present invention has been prepared in densities ranging from about 0.05 to 0.48 g/cc. It can, however, be prepared in lower and higher densities, e.g., ranging from 64 kg/mm$^3$ to 1000 kg/mm$^3$.

After molding, the restorative material is dried and fired by the following preferred procedure. The material is first dried in an oven for 18 hours; the temperature, initially 38° C., is raised at a rate of 11° C. per hour to 104° C., held there for 4 hours, raised again at a rate of 11° C. per hour to 150° C., and held there for 4 hours. The material is taken directly from the drying oven, placed in the firing furnace, and fired. A temperature rise rate of 220° C. per hour or less is required in order to avoid cracking and warping in the udi case of a 15 cm×15 cm×7.5 cm block of material. For larger blocks, slower heating rates may be required. The maximum firing temperature may vary from 1200° C. to 1600° C. depending upon the fiber ratio used, amount of boron nitride, and the final density of the material that is desired.

The temperature rise rate is chosen to permit relatively uniform temperatures to be achieved throughout the material during the process. A faster temperature rise rate causes non-uniform temperatures to be achieved throughout the material during the process. A faster temperature rise rate causes nonuniform strength and density and may cause cracking. Longer or higher temperature firing results in higher shrinkage and related greater resistance to subsequent shrinkage, as well as a shorter lifetime to devitrification under cyclic exposures to high temperatures. The maximum firing temperature is dependent upon the fiber ratio used and the density of the composite desired. The firing time and maximum temperature are selected to allow sufficient shrinkage to achieve stabilization and fiber fusion while not allowing any devitrification.

After firing, the material may be machined to obtain any desired final dimensions. Only about 0.5 cm of the material must be machined off.

The procedure used to prepare the fused fibrous compound material of the present invention, may be varied through a rather broad range with satisfactory results. In one variation, the silica fibers may be borated and prefired prior to use. This process is used to improve the morphological stability and physical properties of the resultant material.

The following examples of fused fibrous compounds are provided to illustrate the invention by describing various embodiments, including its best mode as presently conceived. All proportions used are expressed on a percent by weight basis unless otherwise noted.

EXAMPLE 1

An embodiment of the fused fibrous matrix ceramic material of the present invention having a density of 0.32 g/cc, and opacified with silicon carbide was produced, with 825 grams of silica fibers, 175 grams alumina fiber (average diameter—11 microns, length—0.32 cm), 35 grams 1200 grit silicon carbide, 2.85 grams of boron nitride, 10 milliliters hydrochloric acid, 5 milliliters ammonium hydroxide and deionized water. The silica fibers were washed as in Example 2.

The alumina fibers were placed in a 7,570 ml capacity stainless steel double shell blender with 5,000 grams deionized water and mixed using an intensifier bar for 2½ minutes to disperse the fiber.

The washed silica fibers, dispersed alumina fibers, boron nitride, and silicon carbide were placed in a 28.31 liter stainless steel double shell V-blender. Deionized water was added to bring the total weight to 15,000 grams. The ammonium hydroxide (5 ml) was added to adjust the slurry to basic before mixing. The slurry was mixed, degassed, transferred to a mold and pressed into a billet as in Example 2.

EXAMPLE 2

The materials used were the following: 150 grams aluminasilicate fibers (AS-32, manufactured by 3-M Company containing 80% $Al_2O_3$ and 20% $SiO_2$), 1000 grams of silica fibers (Microquartz 108), 35 grams of 1200 grit silicon carbide, 30 grams of boron nitride, 10 ml of hydrochloric acid, 5 ml of ammonium hydroxide, and deionized water.

The silica fibers were placed in a polyethylene container in 32 liters of deionized water. Hydrochloric acid (10 ml) was added to bring the pH to 3. Pure nitrogen was bubbled through the mixture to agitate the fiber and assist washing. Agitation was continued for two hours. The acidic water was then drained off, fresh deionized water added and the mixture again agitated with pure nitrogen for 15 minutes. The rinsing process was repeated 2 more times which brought the pH to about 6.0.

The aluminasilicate fibers were placed in a 7,570 ml capacity stainless steel double shell blender with 5,000 grams of deionized water and mixed using the intensifier bar for 2½ minutes to disperse the fiber.

The washed silica fibers, dispersed aluminasilicate fibers, boron nitride, and silicon carbide were placed in a 28.31 liter stainless steel double shell V-blender. Deionized water was added to bring the total weight to 18,000 grams. Ammonium hydroxide (5 ml) was added to adjust the slurry to basic before mixing. The slurry was then mixed with the intensifier bar running for 20 minutes, removed from the V-blender and degassed, transferred into a mold, and pressed into a 21.6 cm×21.6 cm×10 cm billet. The top and bottom of the mold were perforated and covered with a 16 mesh aluminum screen to allow the excess water to flow out.

The billet was dried in an oven for 18 hours beginning at 38° C., increased at 11° C. per hour to 104° C., held for four hours at 104° C., increased at 11° C. per hour to 150° C. and held four hours at 150° C. After drying, the billet was transferred to the firing furnace. The furnace temperature was increased at a rate of 220° C. per hour to the firing temperature, 1315° C., where it was held for 1½ hours. After firing, the temperature was decreased at a rate of 220° C. per hour to 980° C. where the furnace was turned off, then allowed to cool to room temperature.

The usefulness of boron oxide in the two-fiber composites of this invention is demonstrated by the following preparations.

EXAMPLE 3

In one run, an experimental mixture was made containing 25% aluminasilicate fibers ("FIBERFRAX H," manufactured by the Carborundum Company, containing 62% $Al_2O_3$ and 38% $SiO_2$) and 75% pure silica fibers ("MICROQUARTZ 108"). The mixture was ground with mortar and pestle and then fired at 1400° C. for 5 hours. The resulting product underwent 48% devitrification. When the aluminasilicate fibers were prefired with boron oxide (85% and 15% respectively) at 1100° C. for 90 minutes and then mixed with the silica fibers and fired as above, the product exhibited no devitrification.

EXAMPLE 4

An acceptable 17 cm×17 cm×7.5 cm billet of material having a density of 0.11 g/cc was produced using 600 grams of silica fibers, 90 grams of aluminaborosilicate fibers (average diameter-11 microns, 0.64 cm long), 10 ml of hydrochloric acid, 5 ml of ammonium hydroxide, and deionized water.

The silica fibers were washed in accordance with the procedure of Example 2. The aluminaborosilicate fibers were dispersed in a 7,570 ml V-blender with 3000 grams of deionized water for 5 minutes. The washed silica fibers, dispersed aluminaborosilicate fibers, and ammonium hydroxide were mixed, with enough deionized water to bring the total weight to 9,000 grams, in a 28.31 liter V-blender for 10 minutes with the intensifier bar running. The slurry was removed from the V-blender, degassed, molded and the resulting billet fired as in Example 2. The billet was then transferred to the firing furnace. The furnace temperature was increased at a rate of 220° C. per hour to the firing temperature, 1260° C., where it was held for 5 hours. After firing, the temperature was decreased at a rate of 220° C. per hour to 980° C., at which point the furnace was turned off and allowed to cool at room temperature. The billet was machined to 17 cm×17 cm×7.5 cm in accordance with usual machining practices.

EXAMPLE 5

An acceptable 17 cm×17 cm×7.5 cm billet of material with yet greater stability toward devitrification than the material produced in example 1, having a density of 0.32 g/cc, and opacified with silicon carbide was produced using 825 grams of silica fibers, 175 grams aluminaborosilicate fibers (average diameter-11 microns, 0.64 cm long), 35 grams of 1200 grit silicon carbide, 10 ml of hydrochloric acid, 5 ml of ammonium hydroxide, 56.8 grams of boron oxide, and deionized water.

The silica fibers were washed in accordance with the procedure of Example 2. The boron oxide was dissolved in 4,000 grams of deionized water (concentration-1.42% boron oxide). The aluminaborosilicate fibers were placed in a stainless steel basket and dipped into the boron oxide solution (the aluminaborosilicate fibers absorbed 7 times their own weight of the boron oxide solution). The fibers with absorbed boron oxide were then dried at 104° C. for 4 hours and calcined at 1100° C. for 1 hour. The "borated" fibers were then placed in a 7,570 ml capacity stainless steel V-blender with 5,000 grams of deionized water and mixed using the intensifier bar for 2½ minutes to disperse the fiber. The washed silica fibers, dispersed "borated" aluminaborosilicate fibers, silicon carbide, and ammonium hydroxide were mixed with enough deionized water to bring the total weight to 15,000 grams, in a one cubic foot V-blender for 20 minutes with the intensifier bar running. The slurry was removed from the V-blender, degassed, molded, dried, fired, and machined, as in Example 1.

EXAMPLE 6

An acceptable 17 cm×17 cm×7.5 cm billet of material with graded properties, having a density of 0.32 g/cc, and opacified with silicon carbide, was produced using 825 grams of silica fibers, 175 grams of aluminaborosilicate fibers (average diameter-11 microns, 0.64 cm long), 35 grams of 1200 grit silicon carbide, 10 ml of hydrochloric acid, 5 ml of ammonium hydroxide, and deionized water.

The silica fibers were washed in accordance with the procedure of Example 2. The aluminaborosilicate fibers were dispersed in a 7,570 ml V-blender with 5000 grams of deionized water for 5 minutes. The washed silica fibers, dispersed aluminaborosilicate fibers, silicon carbide and ammonium hydroxide were mixed with enough deionized water to bring the total weight to 25,000 grams, in a 28.3 liter V-blender for 15 minutes with the intensifier bar running. The slurry was removed from the V-blender, degassed, molded, dried, fired and machined in accordance with the procedure of Example 1.

The resulting billet of material is relatively richer in silica at the top and aluminaborosilicate at the bottom.

EXAMPLE 7

A 17.5 cm×17.5 cm×9 cm material with a temperature capability greater than that of the material of Example 1, having a density of 0.24 g/cc, and opacified with silicon carbide, was produced using 750 grams of aluminaborosilicate fibers (diameter-1 to 3 microns), 250 grams of silica fibers, 35 grams of silicon carbide, 5 ml of ammonium hydroxide, and deionized water. The silica fibers were dispersed in a 7,570 ml V-blender with 5,000 grams of deionized water for 5 minutes.

The dispersed silica fibers, aluminaborosilicate fibers, silicon carbide, and ammonium hydroxide were mixed with enough deionized water to bring the total weight to 18,000 grams, in a 28.31 liter V-blender for 7 minutes with the intensifier bar running. The slurry was removed from the V-blender, degassed, molded, and dried as in Example 2. In the furnace, the temperature was increased at a rate of 220° C. per hour to the firing temperature of 1370° C. where it was held for 1½ hours. After firing, the temperature was decreased at a rate of 220° C. per hour to 980° C., at which point the furnace was turned off and allowed to cool to room temperature. The billet was machined to 17.5 cm×17.5 cm×9 cm in accordance with the usual machining practices.

The preferred alumina fibers are 95.2% pure and are available from ICI Americas, Inc. and marketed as SAF-FRIL™. The preferred diameter for the alumina fibers ranges from 1 to about 15 microns. The preferred silica fibers are 99.7% pure and are available from Schuller (Johns Manville Corp.), Denver, Colo. and marketed as MICRO-QUARTZ 108™ fibers or as Q-FIBER™. These fibers have an average diameter of 1.7 microns. However, silica fibers having diameters ranging from 1 to 6 microns are useful in the present invention.

Also, mixtures of the above-described fibers can be used with other fibers known in the art, e.g., zirconium fibers. In addition, metal fibers and carbon fibers can be utilized by themselves or in combination with other fibers. As stated, the product of the method of the present invention to make the filler/reinforcer of the present invention may comprise as much or greater than 99% silica.

While boron nitride is considered to be the preferred boron source, it is believed that $SiB_x$, $B_4C$, $B_2O_3$, and B and other boron sources can also be used. It is preferred that boron be present in an amount from about 0.4% to about 3% by weight. Boron nitride is believed to be preferred because it is believed, due to its stability, that it permits a more uniform fusion to fiber junction and yields superior bonding and uniform porosity.

In addition, aluminaborosilicate fibers may be used and are available from 3M Company marketed under the tradename AB-312™ which contains 62% (plus/minus 2.0%) $Al_2O_3$, 14% plus/minus 2.0%) $B_2O_3$ and 24% (plus/minus 2.0%) $SiO_2$. These fibers are available and useful in the present invention in diameters ranging from 3 to 12 microns.

The preferred composition comprised of: 21% by weight alumina fiber; 74% by weight silica fiber; 2% by weight (600 grit) silicon carbide; and 2.85% by weight boron nitride is also available commercially in densities to 3 to 64 lbs./ft.$^3$ (plus/minus ¾ lb.) from Lockheed Missiles and Space Company, Inc., Sunnyvale Calif. ("Lockheed") under the trade name "HTP" (High Temperature Performance). For example, Lockheed commercially sells "HTP-12–22" (12 lb/ft.$^3$ density silica/alumina fiber ratio of 78/22), "HTP-12–35" (12 lb./ft.$^3$ density in a silica/alumina fiber ratio of 65/35) and "HTP-12–45" (12 lb./ft.$^3$ density in silica/alumina fiber ratio of 55/45.

Materials Evolution & Development USA, Inc. manufactures the above types of Ultra-low density fused fibrous ceramics under the trade name P.R.I.M.M.™ (Polymeric Rigid Inorganic Matrix Material). Materials Evolution & Development USA, Inc. manufacturers P.R.I.M.M.™ in densities varying from 4 lb./ft.$^3$ to 64 lb./ft.3. P.R.I.M.M.™ material is ground by mortar and pestle, or other grinding mechanism, then sieved into different particulate sizes. An optimum sieved particulate size for P.R.I.M.M.™ material (16 lb/ft$^3$ density) is approximately 180 microns in diameter. However, optimum particle sizes are believed to be dependent upon the particular application and P.R.I.M.M.™ material density, and can range from about 10 microns to about 1000 microns. The preferred particle size of the fused fibrous compound component of the PRIMM™ product of the present invention ranges from about 180 microns to about 250 microns. In addition, in some applications it may be preferable to utilize particles of a smaller size in combination wvith the above particle size range.

The present invention includes the use of radiopacifiers including, but not limited to, barium sulfate, TPB, bismuth, aluminum compounds, metal oxides, and organo-metallic compounds.

The present invention may be utilized with a variety of bone cement systems including, but not limited to, self-activating, light curable, heat curable, self-curing and microwave curing systems.

The density of the PRJMM™ product, i.e., the fused fibrous compound material of the present invention ranges from about 6 lb/ft³ to about 50 lb/ft³, preferably from about 6 lb/ft³ to about 25 lb/ft³, and most preferably from about 6 lb/ft³ to about 16 lb/ft³.

The porosity of the PRIMM™ product, i.e., the fused fibrous compound material of the present invention ranges from about 60% by volume void space and up, preferably the product porosity ranges from about 70% by volume void space and up, and most preferably, the porosity of the fused fibrous compound of the present invention ranges from about 80% by volume void space. For example, 16 lb/ft³ PRIMM™ product of the present invention manufactured utilizing the examples of the present invention comprises approximately 88% by volume void space. Set forth in FIG. 1, the relationship between density and porosity is charted.

The fused fibrous compound of the present invention (PRIMM™ product) preferably has average or mean pore diameters of greater than 10 microns, more preferably over 20 microns.

It is also believed that the addition of a silanation agent is beneficial. The preferred procedure of silanation of fibers is as follows: (1) mix 2 ml silane (Union Carbide A-174) with 2 ml n-propylamine with 196 ml of cyclohexane for 15 minutes; (2) treat fibers for 2 hours in the above prepared solution and stir at room temperature; (3) rinse once with cyclohexane; (4) dry in air at room temperature for 1 hour; and (5) dry at 60° C. for 1 hour. Preferably, the fibers are silanated greater than 90% of the surface area of the fibers.

In addition, it has been found that it may be preferable when adding the fused fibrous compound of the present invention to bone cement systems, to do so under vacuum pressure.

FLEXURAL TESTING OF BONE CEMENT WITH FUSED FIBROUS COMPOUNDS

Figure 2:
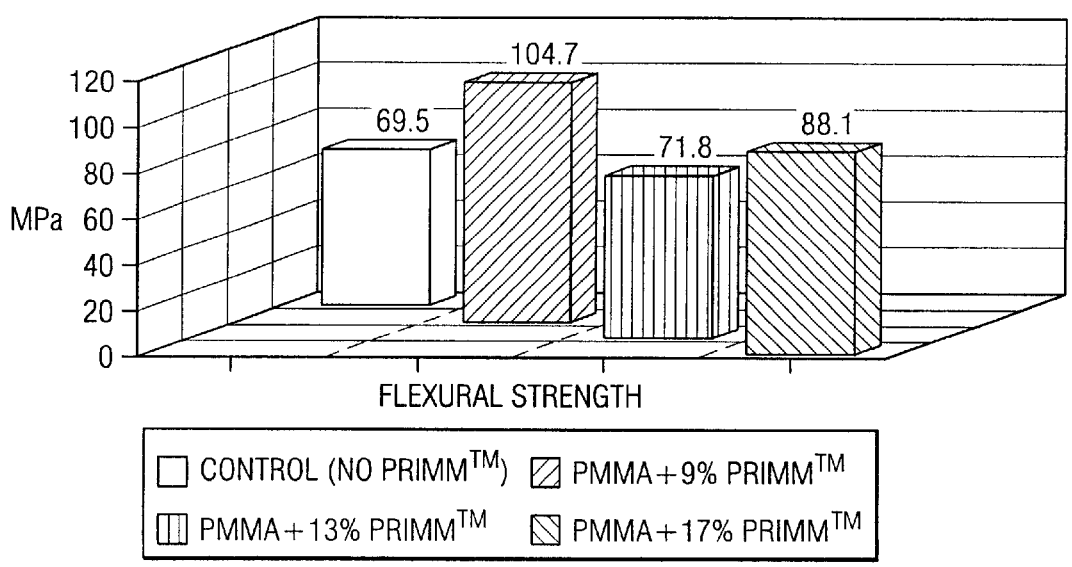
FIG. 2 is a bar graph illustrating the flexural strength of various bone cement compositions reinforced with the fused fibrous compound of the present invention.
Figure 3:
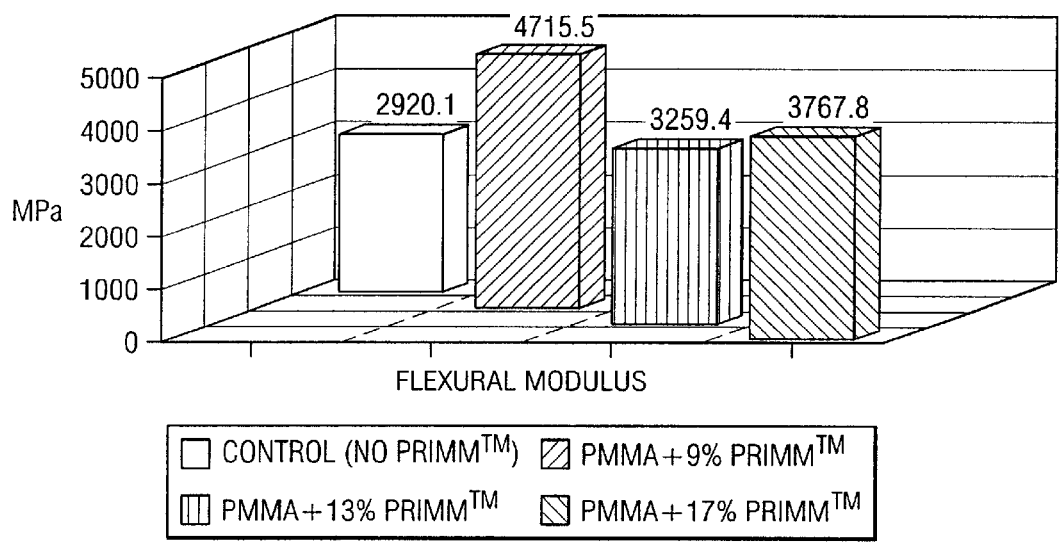
FIG. 3 is a bar graph illustrating the flexural modulus of various bone cement compositions reinforced with the fused fibrous compound of the present invention.

Four sample groups were tested: Control 0% by weight, 10% by weight, 15% by weight, 20% by weight fused fibrous compound. Each group comprised 15 samples with sample dimensions of 2 mm×5 mm×20 mm. The samples were cured in dental stone processiffg flasks made of resin impregnated gypsum rock. Impressions were made in the flasks to the sample dimensions. The flasks were then coated with a thin layer of alcote to facilitate separation of the bone cement samples after cure. The PMMA was mixed with the fused fibrous compound and then monomer liquid added. The samples were hand-mixed for approx. 2 minutes and placed in a mold. The flasks were pressurized under 3000 lb. for about 5 minutes then clamped in place for 5 more minutes. The samples were cured under 2 bar pressure at 45° C. for 15 minutes and then cooled for 30 minutes in lukewarm water. The samples were pried out of the flasks and placed in bags with water and stored for 2 weeks. The samples were each sanded with 320 grit sand paper to the final dimensions prior to mechanical testing. The flexural 3 point bend tests were made on Instrom® machine. The results are summarized below in FIGS. 2 and 3.

SHRINKAGE TESTING ON BONE CEMENT WITH FUSED FIBROUS COMPOUNDS ADDED

Figure 4:
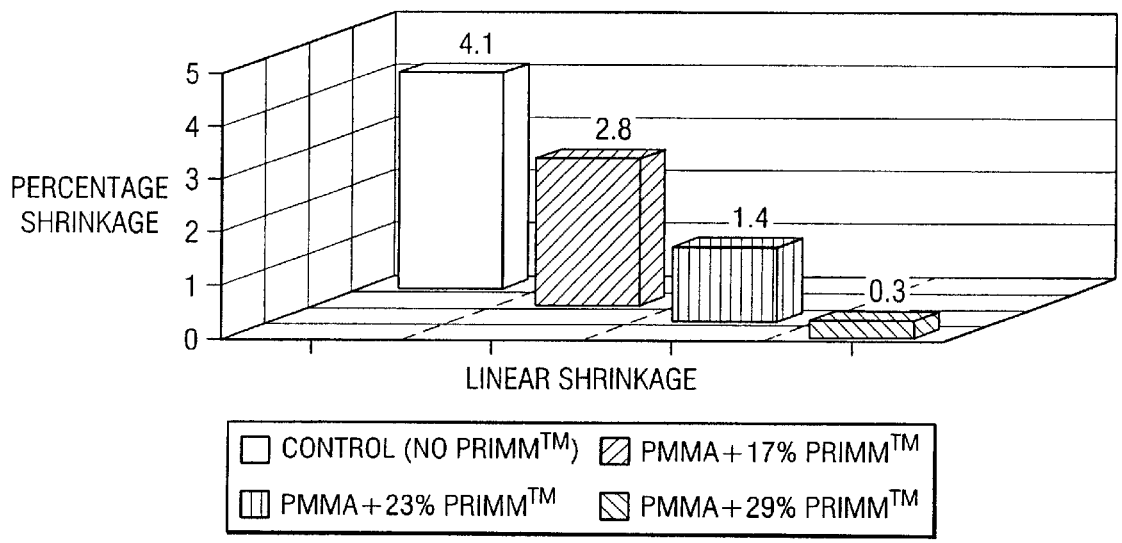
FIG. 4 is a bar graph illustrating the linear shrinkage of bone cement reinforced with the fused fibrous compound of the present invention.

Test Groups: 1 gram PMMA Control 0% fused fibrous compound (PRIMM™); 1 gram PMMA+20%, 30%, and 40% by weight PRIMM® silanated fused fibrous compound in particle form, approximately 180–250 microns. Each group contained 1 gram cement powder, 1 gram liquid monomer and 0, 0.2 grams, 0.3 grams, 0.4 grams of 16 lb./ft. density fused fibrous compound. The percent by weight of fused fibrous compound is based on cement powder component weight and not final bone cement weight. The PMMA and PRIMM were placed on a glass plate and the liquid monomer was added. The samples were mixed for approximately 2.5 minutes then approximately 0.2 grams placed in a ACTA linometer. Shrinkage was recorded for 20–30 minutes per sample. The results are summarized in FIG. 4, wherein the amount of PRIMM™ brand fused fibrous compound is based on total weight of composition.

Figure 5:
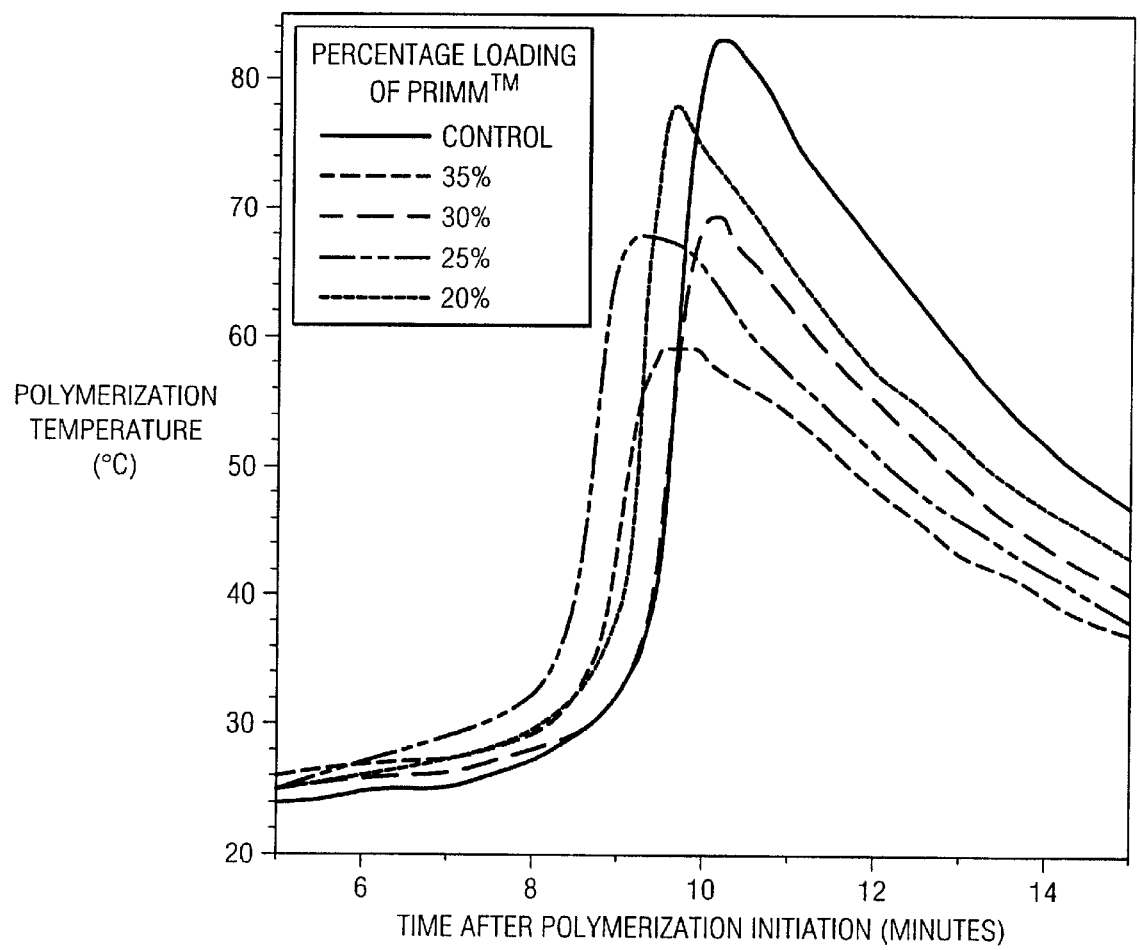
FIG. 5 is a plot illustrating the polymerization temperature versus the time after polymerization initiation of various bone cement compositions reinforced with the fused fibrous compound of the present invention.

The practice of the present invention also reduces the polymerization reaction temperature of PMMA, while as recognized by those skilled in the art, is beneficial and is shown in FIG. 5. A study was conducted to determine the effect of PRIMM™ augmentation on poly(methyl methacrylate) bone cement. The cement was Simplex P (Howmedica), mixed according to instructions which dictated a ratio of 2 grams of powder to 2 ml of liquid. The PRIMM™ material was comprised of silanated 180–250 micron particles at 16 lb/ft³ density. Ten samples were tested by recording the core temperatures with a type K thermocoupler probe. The samples were made by first mixing the cement powder with the PRIMM™ and then mixing in the liquid monomer. The mixing was performed on a glass plate with a plastic spatula for 3–4 minutes until the cement could be molded with gloved hands. The cement was then pressed into a 5 ml glass flask to form a cylindrical sample with a 18 mm diameter and 18–20 mm height. The probe was then inserted all the way through the sample. Both the glass flask and probe tip wvere coated with a lithium grease to encourage extraction from the cement. Temperature recording began at 5 minutes after initial mixing and continued until 15 or 20 minutes.

While the invention has been illustrated and described in detail in the foregoing description, the same is to be considered as illustrative and not restrictive of character, it being understood that only the preferred embodiment has been shown and described and that all changes and modifications that come within the spirit of the invention are desired to be protected.

We claim:

1. An improved bone or dental cement composition comprising:

bone or dental cement; and a fused fibrous compound manufactured from fibers and a fusion source.

2. The cement composition of claim 1 wherein said bone cement comprises polymethylmethacrylate.

3. The cement composition of claim 1 wherein said bone cement comprises methylmethacrylate-styrene.

4. The cement composition of claim 1 wherein said bone cement comprises a radiopacifier.

5. The cement composition of claim 1 wherein said fused fibrous compound is added in the form of particles.

6. The cement composition of claim 5 wherein said fused fibrous compound comprises at least about 60% by volume void space.

7. The cement composition of claim 5 wherein said fused fibrous compound has mean pore diameters of greater than about 10 microns.

8. The cement composition of claim 1 wherein said fused fibrous compound is silanated.

9. The cement composition of claim 1 wherein said fused fibrous compound is manufactured from alumina fibers and silica fibers.

10. The cement composition of claim 1 wherein said fusion source comprises boron.

11. A method for improving a bone or dental cement composition comprising:
adding a fused fibrous compound manufactured from fibers and
a fusion source to the cement composition.

12. The method of claim 11 wherein said fused fibrous compound is added in the form of particles.

13. The method of claim 12 wherein said added fused fibrous compound comprises at least about 60% by volume void space.

14. The method of claim 12 wherein said added fused fibrous compound has mean pore diameters of greater than about 10 microns.

15. The method of claim 11 wherein said added fused fibrous compound is silanated.

16. The method of claim 11 wherein said added fused fibrous compound is manufactured from alumina fibers and silica fibers.

17. The method of claim 11 wherein said fusion source comprises boron.

18. A bone or dental cement treatment kit for bone or tooth repair or other treatment of a bone or tooth defect, said kit comprising: (1) finely divided acrylic polymer, (2) polymerizable liquid acrylic monomers for preparation of bone or dental cement useful in bone or tooth repair or other bone or tooth treatment, and (3) a fused fibrous compound manufactured from fibers and a fusion source.

19. The cement treatment kit of claim 18 wherein said polymer comprises polymethylmethacrylate.

20. The cement treatment kit of claim 18 wherein said acrylic monomers comprise methylmethacrylate-styrene-copolymer.

21. The cement treatment kit of claim 18 further comprising a radiopacifier.

22. The cement treatment kit of claim 18 wherein said fused fibrous compound is added in the form of particles.

23. The cement treatment kit of claim 22 wherein said fused fibrous compound comprises at least about 60% by volume void space.

24. The cement treatment kit of claim 22 wherein said fused fibrous compound has mean pore diameters of greater than about 10 microns.

25. The cement treatment kit of claim 18 wherein said fused fibrous compound is silanated.

26. The cement treatment kit of claim 18 wherein said fused fibrous compound is manufactured from alumina fibers and silica fibers.

* * * * *